US010386655B2

(12) United States Patent
Lee et al.

(10) Patent No.: US 10,386,655 B2
(45) Date of Patent: Aug. 20, 2019

(54) DEVICE, SYSTEM AND METHOD FOR DETECTING OVERLAP OF AN OPHTHALMIC DEVICE BY AN EYELID

(71) Applicant: Verily Life Sciences LLC, Mountain View, CA (US)

(72) Inventors: Shungneng Lee, Sunnyvale, CA (US); Uei-ming Jow, San Jose, CA (US); Nathan Pletcher, Mountain View, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 383 days.

(21) Appl. No.: 15/221,522

(22) Filed: Jul. 27, 2016

(65) Prior Publication Data
US 2018/0031867 A1 Feb. 1, 2018

(51) Int. Cl.
*G01N 27/00* (2006.01)
*G08B 19/00* (2006.01)
(Continued)

(52) U.S. Cl.
CPC ............ *G02C 7/083* (2013.01); *A61B 3/0025* (2013.01); *A61B 3/10* (2013.01); *A61B 3/113* (2013.01);
(Continued)

(58) Field of Classification Search
CPC .......... G02C 7/083; G02C 11/10; G02C 7/04; A61B 3/10; A61B 3/0025; A61B 3/113; G06F 3/044; G06F 3/013
(Continued)

(56) References Cited

U.S. PATENT DOCUMENTS 6,423,001 B1 7/2002 Abreu
8,857,983 B2 10/2014 Pugh et al.
(Continued)

FOREIGN PATENT DOCUMENTS

EP 2772789 A1 9/2014
EP 2979622 A1 2/2016
(Continued)

OTHER PUBLICATIONS

PCT/US2017/040270, International Search Report and Written Opinion of the International Searching Authority, dated Nov. 3, 2017, 14 pages.

*Primary Examiner* — Richard Tan
(74) *Attorney, Agent, or Firm* — Christense O'Connor Johnson Kindness PLLC

(57) ABSTRACT

Techniques and mechanisms for sensing an overlap of an ophthalmic device by an eyelid of a user while the ophthalmic device is disposed in or on an eye of the user. In an embodiment, a circuit, disposed in a sealed enclosure of the ophthalmic device, interacts via an electromagnetic field with a film of tear fluid that is formed on the ophthalmic device. Based on the electromagnetic interaction, an oscillation characteristic of the circuit is evaluated. The oscillation characteristic varies with a resistance that is due in part to an eyelid of the user overlapping at least some portion of the ophthalmic device. Based on the evaluated oscillation characteristic, an amount of the eyelid overlap is determined by circuitry of the ophthalmic device. In another embodiment, the amount of eyelid overlap is used to determine one or more characteristics of gazing by the user's eye.

27 Claims, 7 Drawing Sheets

(51) Int. Cl.
  *G08B 21/00*  (2006.01)
  *G01J 5/00*  (2006.01)
  *G01K 7/00*  (2006.01)
  *G05D 23/20*  (2006.01)
  *G08B 13/18*  (2006.01)
  *G08B 27/00*  (2006.01)
  *G02C 7/08*  (2006.01)
  *A61B 3/00*  (2006.01)
  *A61B 3/113*  (2006.01)
  *G02C 7/04*  (2006.01)
  *G02C 11/00*  (2006.01)
  *A61B 3/10*  (2006.01)
  *G06F 3/01*  (2006.01)
(52) U.S. Cl.
  CPC ............... *G02C 7/04* (2013.01); *G02C 11/10* (2013.01); *G06F 3/013* (2013.01)
(58) Field of Classification Search
  USPC .......................................................... 307/66
  See application file for complete search history.

(56) References Cited

U.S. PATENT DOCUMENTS

| | | |
|---|---|---|
| 2014/0240655 A1 | 8/2014 | Pugh et al. |
| 2014/0350376 A1 | 11/2014 | Nachum |
| 2015/0057516 A1 | 11/2015 | Mujeeb-U-Rahman et al. |
| 2015/0362751 A1* | 12/2015 | Biederman ............ G02C 7/083 349/13 |
| 2017/0092235 A1 | 3/2017 | Osman et al. |
| 2018/0217402 A1 | 8/2018 | Larmagnac et al. |

FOREIGN PATENT DOCUMENTS

| | | |
|---|---|---|
| WO | 3088867 A2 | 10/2003 |
| WO | 2015041715 A1 | 3/2015 |
| WO | 2015191241 A1 | 12/2015 |

\* cited by examiner

DEVICE, SYSTEM AND METHOD FOR DETECTING OVERLAP OF AN OPHTHALMIC DEVICE BY AN EYELID

BACKGROUND

1. Technical Field

This disclosure relates generally to the field of optics, and in particular but not exclusively, relates to contact lenses.

2. Background Art

Accommodation is a process by which the eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and applies a force on the elastic lens during muscle contractions that change the focal point of the elastic lens.

As an individual ages, increased stiffness of eyes' lenses tends to decrease the effectiveness of the ciliary muscles in providing accommodation. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages.

Recent technologies have begun to provide for various devices that operate in or on a human eye to aid the visual focus of a user. For some types of these devices, an accommodating lens includes one or more elements and circuitry to apply an electrical signal to change a focusing power of the one or more elements. Determining when to change such focusing power is often based on a direction of a gaze by a user of the optical device. As the capabilities of accommodation-capable optical devices continue to increase, there is expected to be an increased demand for such optical devices to provide accurate tracking of direction of gaze by a user.

BRIEF DESCRIPTION OF THE DRAWINGS

The various embodiments of the present invention are illustrated by way of example, and not by way of limitation, in the figures of the accompanying drawings and in which.

DETAILED DESCRIPTION

Figure 1:
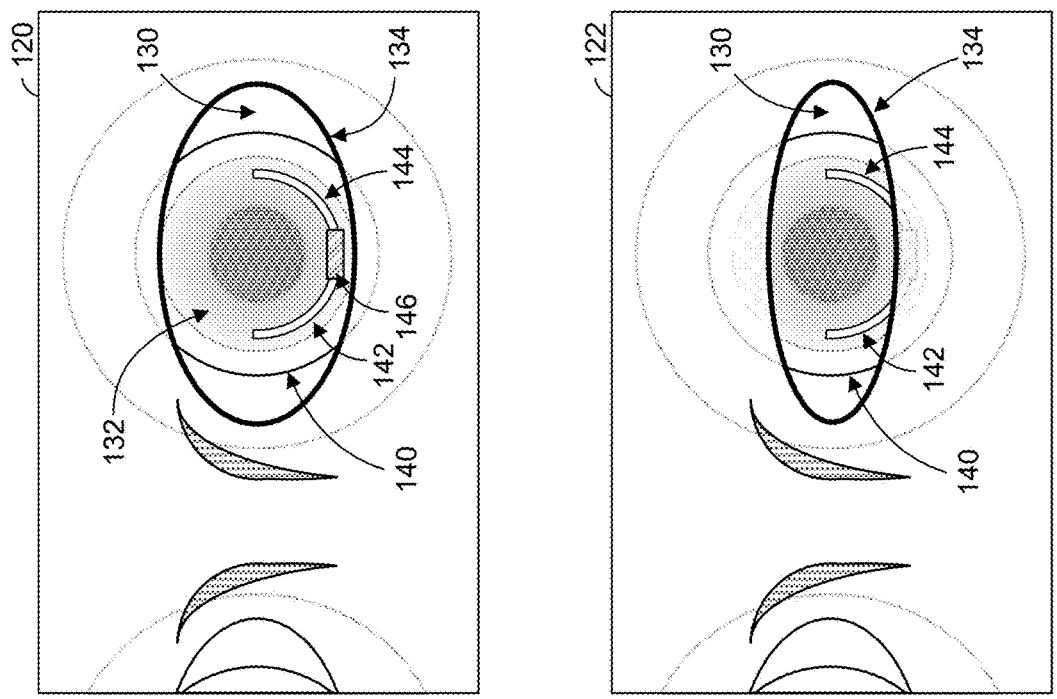
FIG. 1 shows a functional block diagram illustrating elements of an ophthalmic device to detect overlap of an ophthalmic device according to an embodiment.
Figure 1:
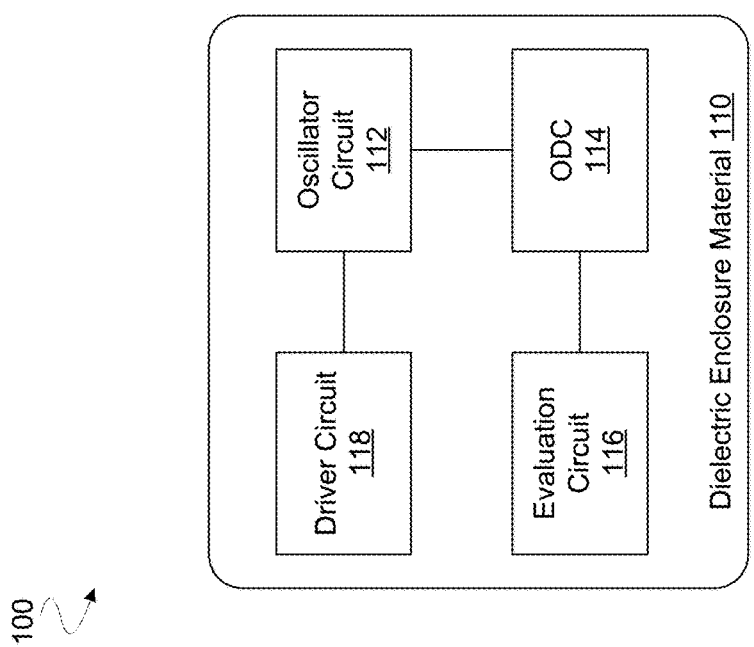

Embodiments of an ophthalmic lens system including mechanisms to detect eyelid overlap are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some designs for eye-mountable devices, the sensing of eyelid overlap is performed by photodetection to determine whether light is being prevented from reaching a photodiode that is disposed in an eye-mountable device. This use of light-based sensing has certain drawbacks—e.g., due to the wide dynamic range of ambient light in many typical environments. As an alternative to photodetector sensing, other eye-mountable device designs rely on a type of capacitive sensing, similar to that used in touchscreen technologies, to detect a capacitance of an eyelid. However, the inventors have observed that this type of capacitive sensing tends to have problems distinguishing a user's eyelid from the presence of a film of tear fluid (or "tear film") over the user's eye. The inventors have further observed that the conductivity of a tear film tends to block, or severely limit, the impact that a capacitance of a user's eyelid may otherwise have on dielectric and/or electric field properties of a fully-encapsulated capacitance sensor within an eye-mountable device (EMD), such as a contact lens, or other such ophthalmic device.

Certain embodiments result from a realization by the inventors that a tear film is a source of error in detecting eyelid capacitance, and that another type of circuit design may be adapted to efficiently distinguish between a tear film and eyelid overlap. Some embodiments detect a resistivity (and/or a change thereof) that is due to a combination of resistances each provided by different respective one of a tear film and a user's eyelid.

A sensor circuit according to an embodiment may function as an oscillator based at least in part on an electromagnetic interaction between the sensor circuit and the tear film. Such oscillation may be further based on additional electromagnetic interaction between the circuit and a portion of the eyelid (if any) that overlaps the sensor circuit. For example, a frequency of resonance by the sensor circuit may be based at least in part on inductive structures and capacitive structures of the ophthalmic device. By evaluating operational characteristics of the sensor circuit, the various impedances of such inductive structures and capacitive structures may be accounted for, thus enabling detection of a resistive (real domain) component of impedance that is attributable to a tear film and any overlapping eyelid portion. Variation of such a resistive component may be proportional to an amount that the eyelid overlaps at least some portion of the sensor mechanism. By way of illustration and not limitation, a circuit of the sensor mechanism may, at a given time, be characterized by a minimum amount of current needed (at least at that time) to enable signal oscillation with that circuit. The required minimum amount of current may change over time with changes to the external environment adjoining the ophthalmic device—e.g., in proportion to a varying resistance that is provided by the tear film and any overlapping eyelid portion.

One benefit of various embodiments is the full encapsulation of a sensor within an ophthalmic device. By being fully encapsulated in a dielectric encapsulation material, electrodes and/or other sensor structures of some embodiments are not electrically exposed at a surface of an ophthalmic device. Such encapsulation may provide for significant improvements in the lifetime of an ophthalmic device, its fit on a user's eye, its resistance to moisture ingress and/or the like.

FIG. 1 is a functional block diagram of an ophthalmic device 100, such as a smart contact lens, comprising circuitry to detect whether at least a portion of ophthalmic device 100 is being overlapped by an eyelid of a user. Detection of this type of overlap (for brevity, referred to herein simply as "eyelid overlap") may be used, for example, in communications with a remote device, to evaluate a state of the user, to determine an operation to be performed by an accommodation actuator and/or the like.

Embodiments of ophthalmic device 100 may include power supply circuitry, control electronics and an eyelid overlap sensor—and, in some embodiments, an accommodation actuator and/or an antenna—all embedded within an enclosure material formed to be contact mounted to an eye. The enclosure material, represented by the illustrative dielectric enclosure material 110, may function as a light transmissive lensing material and may form, at least in part, a sealed enclosure in which is disposed circuitry of ophthalmic device 100. The dielectric enclosure material 110 may be fabricated of a variety of materials compatible for direct contact with a human eye, such as a polymeric material, a hydrogel, PMMA, silicone based polymers (e.g., fluoro-silicon acrylate), or otherwise. The dielectric enclosure material 110 may be in the form of a round lens with a concave curvature configured to mount to a corneal surface of an eye. The electronics may be disposed upon a substrate embedded within the one or more enclosure materials near a periphery of ophthalmic device 100 to avoid interference with incident light received closer to the central region of the cornea.

Ophthalmic device 100 is one example of an embodiment comprising a lens (e.g., including the illustrative dielectric enclosure material 110) forming a sealed enclosure, wherein circuitry disposed in the sealed enclosure is operable to detect an amount by which an eyelid of a user overlaps ophthalmic device 100. In the illustrative embodiment shown, such circuitry includes an oscillator circuit 112 comprising a first electrode portion and a second electrode portion (not shown) that variously extend along respective regions of ophthalmic device 100. The first electrode portion and the second electrode portion may be different respective portions of an inductive loop structure. Alternatively, the first electrode portion may be coupled to the second electrode portion via only one end of the first electrode portion.

Oscillator circuit 112 may variously operate at different times under various conditions to facilitate eyelid overlap sensor functionality. For example, the first electrode portion and the second electrode portion may be configured to interact electromagnetically—through the dielectric enclosure material 110—with an environment that is external to ophthalmic device 100. The environment may include some or all of a cornea of the user's eye, a tear film that adjoins the dielectric enclosure material 110 and, at times, some portion of an eyelid that might be overlapping ophthalmic device 100. In some embodiments, oscillator circuit 112 may be operated to induce an oscillation state with the first electrode portion and the second electrode portion.

For example, a driver circuit 118 of ophthalmic device 100 may also be disposed within the sealed enclosure. Driver circuit 118 may be coupled to drive oscillator circuit 112 with a signal that causes the first electrode portion and the second electrode portion to emit an electromagnetic field. Interaction between the electromagnetic field and an environment (not shown) external to the lens—e.g., the environment including a tear film on the lens and/or an eyelid of a user—may contribute to a signal oscillation state, or "oscillation response," at oscillator circuit 112. The electromagnetic interaction may result in oscillator circuit 112 exhibiting one or more signal characteristics that are indicative of an amount of eyelid overlap. An oscillation detector circuit (ODC) 114, also disposed within the sealed enclosure, may be coupled to monitor for a threshold state of oscillation of oscillator circuit 112. As used herein, "threshold state of oscillation" refers to an oscillation response that results from a perturbation of a first state at the oscillator circuit, but where that first state is near an alternative second state wherein no such oscillation response would result from such perturbation.

In an embodiment, driver circuit 118 includes initialization circuitry (not shown) coupled to successively configure multiple initialization states of oscillator circuit 112. In such an embodiment, driver circuit 118 may further comprise a pulse generator (not shown) coupled to provide, for each of the multiple initialization states, a respective perturbation of the initialization state, wherein ODC 114 monitors oscillator circuit 112 to detect for any occurrence of a given oscillation response to the respective perturbation. ODC 114 may be coupled to determine one or more signal characteristics at oscillator circuit 112—e.g., wherein ODC 114 detects an amount of resistance that is provided, in part, by a tear film over ophthalmic device 100 and, at different times, a varying amount resistance due to an eyelid that overlaps at least some part of ophthalmic device 100. Detecting the resistance may include detecting a threshold amount of current for starting up an oscillation with oscillator circuit 112 (wherein the threshold amount of input current changes depending at least in part on an amount of eyelid overlap).

ODC 114 may include or otherwise have access to memory resources (not shown) that store, for example, criteria information used to determine whether an output of oscillator circuit 112 qualifies as an oscillation response to a corresponding perturbation. Such criteria information may include a threshold minimum number of transitions by an output from oscillator circuit 112 within a defined time period. Alternatively or in addition, criteria information may include a threshold minimum amplitude of the output from oscillator circuit 112. ODC 114 may monitor oscillator circuit 112 for the threshold state of oscillation based on the criteria information. For example, detecting for such an oscillation response may include ODC 114 identifying whether an amplitude of an output by oscillator circuit is greater than (or equal to, in some embodiments) some threshold minimum amplitude. In another embodiment, detecting for an oscillation response includes ODC 114 counting transitions (e.g., through a threshold voltage or current level) by an output of oscillator circuit 112 during some predefined sample period. The total counted number of the transitions may then be compared to some predefined threshold minimum number of transitions for the output to qualify as an oscillation response.

An evaluation circuit 116 of ophthalmic device 100, disposed within the sealed enclosure, may be coupled to ODC 114 to receive an indication of the threshold state of oscillation and to correlate the indication of the threshold state of oscillation with an amount of eyelid overlap. For example, memory resources of ophthalmic device 100 may store reference information that corresponds multiple initialization states (and/or corresponding oscillation responses) of oscillator circuit 112 each with a different respective amount of eyelid overlap. In such an embodiment, ODC 114 may communicate to evaluation circuit 116 an indication of a threshold initialization state for producing an oscillation response. Based on such an indication, evaluation circuit 116 may perform an evaluation—e.g., including a lookup of the reference information—to identify an amount of eyelid overlap that corresponds to the threshold initialization state. Evaluation circuit 116 may then generate one or more signals identifying the amount of eyelid overlap.

The threshold oscillation state of oscillator circuit 112 may change over time based on environmental conditions including, for example, an extent to which an eyelid of a user overlaps ophthalmic device 100. In one embodiment, ODC 114 successively performs multiple test rounds over time, each test round to detect a respective current threshold oscillation state of oscillator circuit 112. The test rounds may each include multiple sample cycles each corresponding to a different respective initialization state of oscillator circuit 112. For a given test round of the test rounds, the multiple sample cycles of the given test round may each correspond to a different respective value of an input to be provided to oscillator circuit 112 with driver circuit 118. For example, the input may include a current provided by the current source of driver circuit 118. In another embodiment, the input includes a voltage that biases oscillator circuit 112. The performance of a given test round may include dynamically selecting an initialization state (e.g., a level of an input) for a sample cycle to be performed, wherein the selecting is based on a result of a preceding sample cycle and a binary search algorithm.

As shown in inset 120 of FIG. 1, one embodiment may include an ophthalmic device 140 (such as ophthalmic device 100) configured to be disposed in or on an eye 130 of a user—e.g., where ophthalmic device 140 is a contact lens to cover some or all of an iris 132 of eye 130. Movement of eye 130 and/or an eyelid 134 of the user may result in eyelid 134 overlapping ophthalmic device 140 by different amounts at different times. In an embodiment, ophthalmic device 140 includes a sensor mechanism to detect an amount of overlap by eyelid 134—e.g., based on a change of resistance that might result from any such overlap.

By way of illustration and not limitation, such a sensor mechanism may include a circuit (such as oscillator circuit 112) including a first electrode portion 142 and a second electrode portion 144 that variously extend in a light transmissive, dielectric enclosure material of ophthalmic device 140. Electrode portions 142, 144 may be configured to function as respective electrode portions each to interact electromagnetically with a tear film that extends over ophthalmic device 140 (e.g., where at least part of the tear film is between ophthalmic device 140 and eyelid 134). Electrode portions 142, 144 may function as electrode portions that variously extend each in a respective arc across at least some angular segment (e.g. at least 30°) of ophthalmic device 140—e.g., wherein such electrode portions connect to one another to form at least part of a loop structure of the same single electrode. The arcing electrode portions may be located near a periphery of ophthalmic device 140 (e.g., away from a center thereof) to mitigate interference with the user's viewing. For example, one or both of electrode portions 142, 144 may be located so that at least a portion of the electrode portions 142, 144 is closer to a periphery of ophthalmic device 140 than to a center of ophthalmic device 140.

In some embodiments, one or both of electrode portions 142, 144 are further configured to interact electromagnetically with another tear film that extends under ophthalmic device 140 (e.g., between eye 130 and ophthalmic device 140). As shown in inset 122, eyelid 134 and/or eye 140 may move over time, resulting in different amounts by which eyelid 134 overlaps one or both of electrode portions 142, 144. Different amounts of overlap by eyelid 134 may affect one or more signal characteristics associated with an electromagnetic interaction by electrode portions 142, 144 with the environment that is external to ophthalmic device 100.

In one embodiment, the circuit including electrode portions 142, 144 may be operated to exhibit signal oscillation that includes and/or is in response to one or more such electromagnetic interactions. Detection of eyelid overlap may be based on testing to determine a threshold condition for inducing such oscillation. For example, integrated circuitry 146 of ophthalmic device 140 (e.g., the integrated circuitry 146 including ODC 114 and/or evaluation circuit 116) may determine a threshold amount of a bias voltage, an input current and/or other input to facilitate oscillation. Based on both the detected threshold amount and some predetermined reference information, integrated circuitry 146 may identify an amount by which eyelid 134 overlaps some portion of ophthalmic device 140.

Electrode portions 142, 144 may form respective portions of one or more capacitive links that variously extend each through the encapsulating dielectric material to a tear film that is itself to function as an electrode coupled to the capacitive links. Portions of the tear film may each be directly above a respective one of electrode portions 142, 144—e.g., wherein another portion of tear film (between such portions) exhibits a characteristic resistance. The effect of such resistance on the circuit including electrode portions 142, 144 may change over time with the changing external environment, depending at least in part on the amount of any eyelid portion that is disposed upon the tear film. For embodiments where electrode portions 142, 144 are electrodes that are distinct from one another, electrode portions 142, 144 may be coupled to an inductor that, for example, is disposed on an application specific integrated circuit (ASIC) such as integrated circuitry 146.

In the illustrative embodiment shown, electrode portions 142, 144 are two distinct electrode portions arranged in a U-shaped configuration that extends partially around a center of ophthalmic device 140. The EMD 550 of FIG. 5B, for example, illustrates an embodiment having a similar configuration wherein electrode portions 570, 572 form respective electrodes that are distinct from one another. However, ophthalmic device 140 may include any of a variety of additional or alternative configurations of electrode portions, in various embodiments. For example, electrode portions 142, 144 may be different respective portions of a single electrode that couples to integrated circuitry 146 at two points and that encircles the center of ophthalmic device 140. In such an embodiment, the electrode portions 142, 144 may be different respective portions of a ring electrode that provides at least some inductance of the circuit. In another example embodiment of the EMD 500 shown in FIG. 5A, electrode portions 522, 524 form different respective portions of a single conductive loop structure 520. A parasitic capacitance may also be provided along a length of such a ring electrode—e.g., where electromagnetic field lines are to extend through the dielectric encapsulation material toward an adjoining tear film. The tear film itself may function as a resistor that is coupled in series with the parasitic capacitance, and in parallel with the inductance of the ring electrode, to enable oscillation of the circuit including electrode portions 142, 144.

Figure 2:
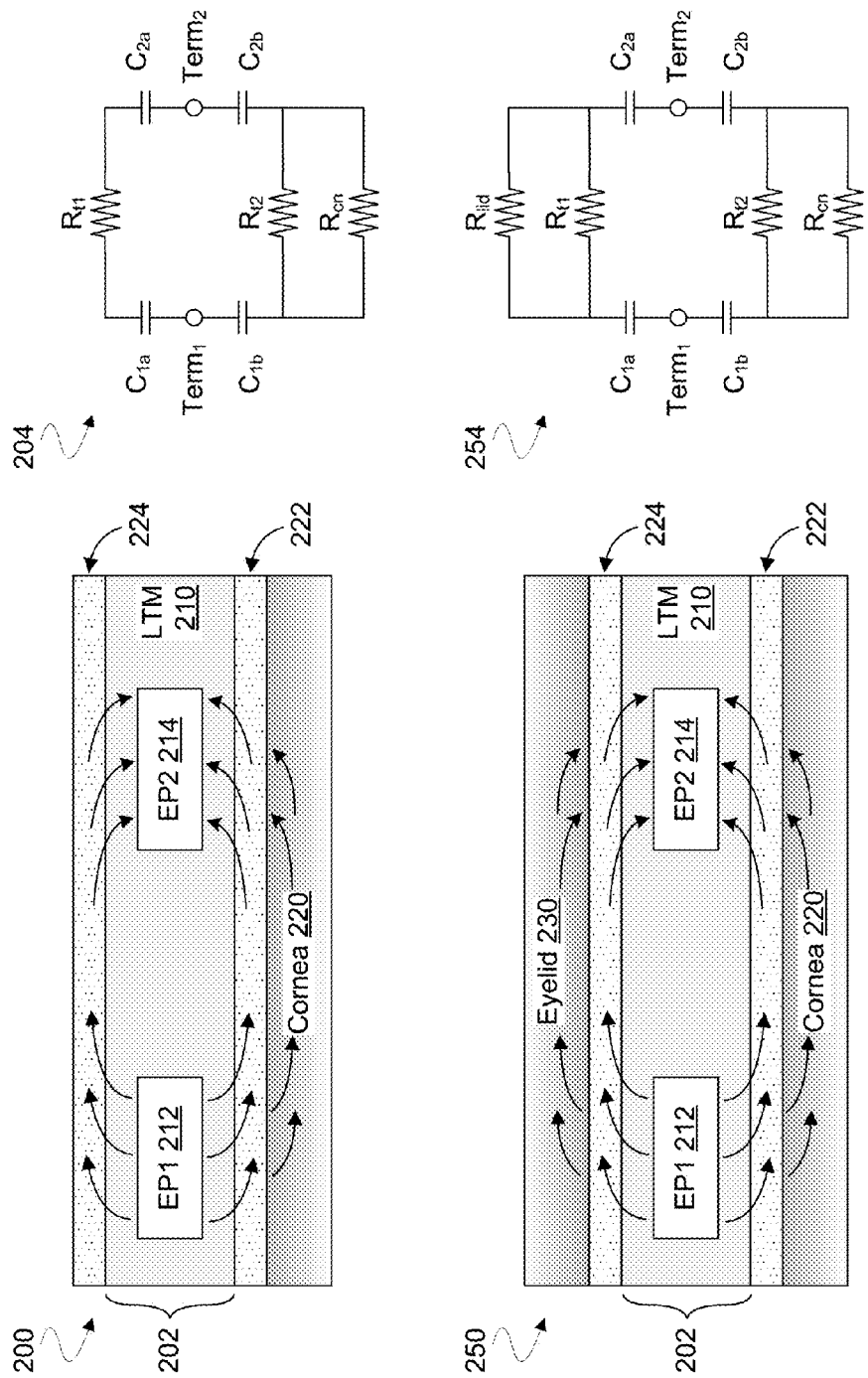
FIG. 2 shows cross-sectional views and circuit diagrams variously representing an ophthalmic device to detect, according to an embodiment, overlap by an eyelid of a user.

FIG. 2 shows cross-sectional views—during respective states 200, 250—of a user's eye while that user is wearing an ophthalmic device 202 according to an embodiment. Ophthalmic device 202 may include some or all of the features of one of ophthalmic devices 100, 140, for example.

A sensor circuit (e.g., having some or all features of oscillator circuit 112) may be fully encapsulated in a silicone, a rigid gas permeable (RGP) material, or other dielectric encapsulation material of the ophthalmic device 202. Such encapsulation may aid in preventing moisture ingress during the operating lifetime of ophthalmic device 202. Operation of the sensor circuit may exploit the formation of a capacitive link which extends between a fully encapsulated electrode of the sensor circuit and the surface of a tear film. For brevity, this type of capacitive link is referred to herein as "lens capacitance."

A tear film may be conductive of a current that is induced with the sensor circuit of ophthalmic device 202. The effect of such conductivity on operational characteristics of the sensor circuit may change over time with the changing external environment—e.g., due to any additional conductance of a biological material (such as the eyelid) that comes in contact with the tear film. The extent to which an eyelid overlaps the sensor circuit may affect a resistivity of a current path that is in parallel with the tear film. In order to efficiently measure bio-conductance/bio-resistance of a tear film (in combination with that resulting from any eyelid overlap), some embodiments variously provide an inductive element that, for example, is coupled in parallel with an in-series combination of lens capacitance and a resistance of the tear film. During a resonance state of the sensor circuit, such an inductance element may cancel out or otherwise significantly offset an impedance provided with the lens capacitance. Therefore, at the resonance state of the sensor circuit, the frequency of oscillation may be automatically determined as a resonance for a combination of the inductor and the lens capacitance, effectively exposing a total amount of resistance provided by the tear film and eyelid (if present)—e.g., where sensing of such resistance is not obscured by the impedance of the lens capacitance. This resistance may directly correlate with, and be sensed by determining, a minimum amount of current needed to startup oscillation of the sensor circuit.

Figure 5B:
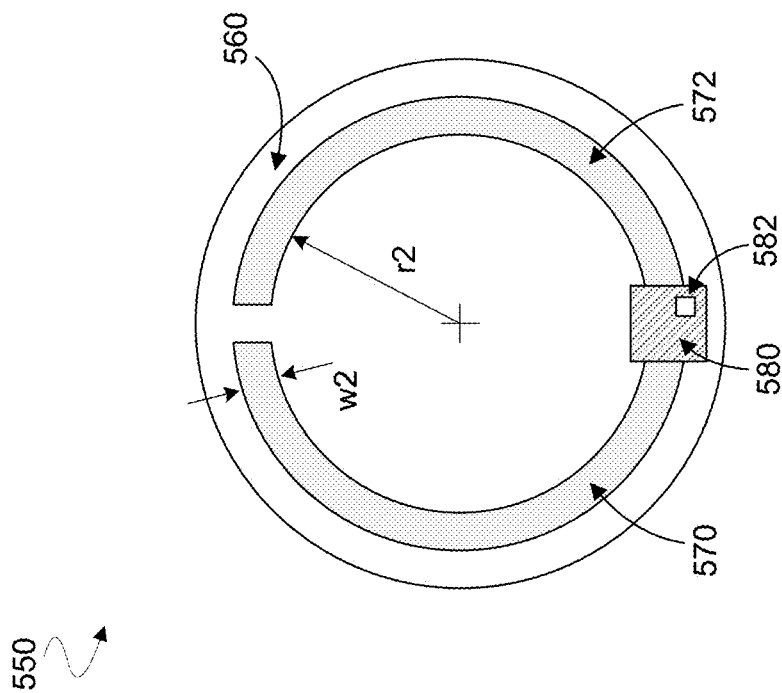
FIGS. 5A, 5B are top views each of a respective eye-mountable ophthalmic device, in accordance with a corresponding embodiment.
Figure 5A:
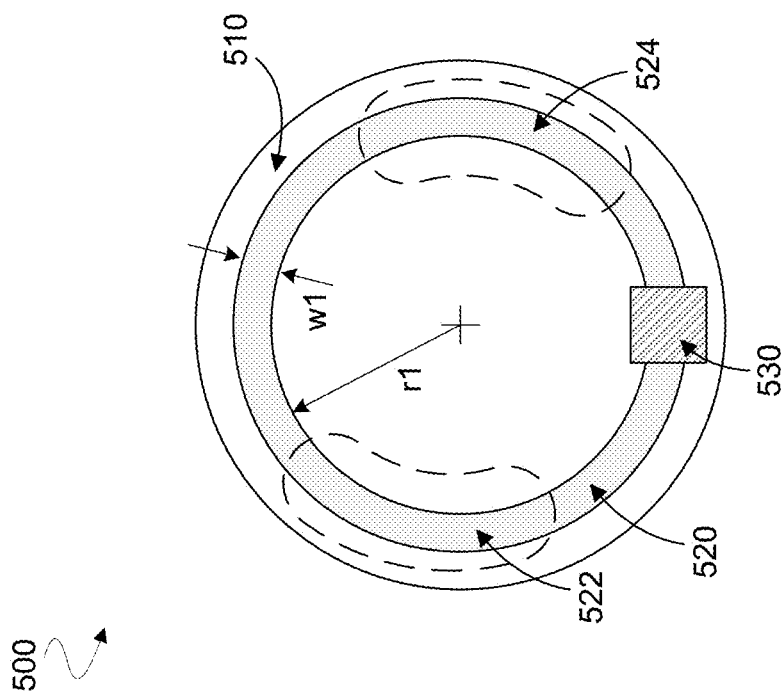

An inductance element of ophthalmic device 202 may be formed, for example, with a ring-like configuration of an electrode structure that also contributes to lens capacitance (as illustrated in FIG. 5A, for example). Alternatively or in addition, an inductor may be embedded on-chip in an IC chip of ophthalmic device 202—e.g., wherein the sensor circuit further comprises at least two distinct electrodes to variously contribute to lens capacitance. In some embodiments, the sensor circuit may include or couple to an oscillator circuit that is configured to induce oscillation (resonance) with electrode structures that contribute to the lens capacitance. An amount of current required to achieve oscillation startup may be proportional to the amount of resistance across at least a portion of the tear film. At a time when an eyelid overlaps at least a portion of the sensor circuit, the resistance across an underlying portion of tear film may be relatively low, as compared to when there is relatively less (or no) eyelid overlap. A level of such bio-resistance may be measured in some embodiments by determining a threshold amount of current required to start oscillator of sensor circuitry.

During states 200, 250, ophthalmic device 202 is disposed on a cornea 220 of the user's eye, wherein a tear film 222 extends between a cornea 220 of the eye and a light transmissive dielectric enclosure material LTM 210 of ophthalmic device 202. Another tear film 224 may extend across an upper surface of LTM 210. State 200 represents a time when, as compared to state 250, an eye of the user is relatively more open. During state 250, an eyelid 230 of the user overlaps a surface area of LTM 210 that is larger than any area of LTM 210 that might be overlapped by eyelid 230 during state 200.

To facilitate detection eyelid overlap, a circuit (e.g., oscillator circuit 112) of ophthalmic device 202 may include a first electrode portion EP1 212 and a second electrode portion EP2 214 that variously extend within LTM 210. In one illustrative embodiment, LTM 210 separates tear film 224 from a closest side of EP1 212 (and/or from a closest side of EP2 214) by a distance that, for example, is in a range from 0.20 millimeters (mm) to 0.4 mm. However, EP1 212 and/or EP2 214 may be separated by any of various smaller distances or larger distances, in various embodiments. EP1 212, EP2 214 may be coupled to facilitate various electromagnetic interactions—via LTM 210—with structures external to ophthalmic device 202. By way of illustration and not limitation, operation of the circuit during state 200 may provide for various current paths from EP1 212 to EP2 214. Such current paths may include, for example, a current path through LTM 210 and along tear film 224, and another current path through LTM 210 and along a length of tear film 222. Such operation of the circuit during state 200 may further provide a current path through LTM 210, through tear film 222 and along a length of cornea 220. Due to the increased overlap of eyelid 230, similar operation of the circuit during state 250 may further provide for an additional current path from EP1 212 to EP2 214, where the path extends through LTM 210, through tear film 224 and along a length of eyelid 230. Such an additional current path may be prevented or otherwise mitigated by a relatively smaller overlap of (e.g., an absence of) eyelid 230 during state 200.

Some embodiments result from a realization that an ophthalmic device may be configured to interact with external structures, wherein the external structures and components of the ophthalmic device may be modeled, collectively, as a circuit that can be tested for detecting a resistance attributable to eyelid overlap. For example, the current paths variously provided during states 200, 250 may be represented by the respective circuits 204, 254 shown in FIG. 2. Circuit 204, which represents a model of state 200, includes a series-coupled arrangement of a capacitance $C_{1a}$, a resistance $R_{t1}$ of tear film 224 and a capacitance $C_{1b}$. $C_{1a}$ represents a lens capacitance provided by a portion of LTM 210 in the area between a top side of EP1 212 and tear film 224. $C_{1b}$ represents a lens capacitance provided by a portion of LTM 210 in the area between a bottom side of EP1 212 and tear film 222. Circuit 204 includes additional circuitry coupled in parallel with the in-series arrangement of $C_{1a}$, $R_{t1}$ and $C_{1b}$. This additional circuitry comprises a lens capacitance $C_{2a}$ and a lens capacitance $C_{2b}$ coupled in series with a parallel-coupled arrangement of a resistance Rte of tear film 222 and a resistance $R_{cn}$ of cornea 220. $C_{2a}$ represents a lens capacitance provided by a portion of LTM 210 in the area between a top side of EP2 214 and tear film 224, and $C_{2b}$ represents a lens capacitance provided by a portion of LTM 210 in the area between a bottom side of EP2 214 and tear film 222.

Circuit 254, which represents a model of state 250, includes the circuitry of circuit 202, in addition to a non-infinite resistance $R_{lid}$ coupled in parallel with the resistance $R_{t1}$ of tear film 224. $R_{lid}$, which represents a resistance provided by eyelid 230, may vary overtime according to the amount to which eyelid 230 overlaps a region including EP1 212 and EP2 214. The absence of $R_{lid}$ in circuit 204 represents an effectively infinite resistance (e.g., an open circuit) coupled across $R_{t1}$ due to an absence of overlap by eyelid 230.

Circuits 204, 254 may each include, or comprise part of, a RLC circuit configured to exhibit, at least under some conditions, one or more signal oscillation (or "resonance") characteristics. For example, EP1 212 and EP2 214 may be different respective portions of a conductor that loops within LTM 210 to form an inductor (not shown) of circuits 204, 254. In such an embodiment, EP1 212 and EP2 214 contribute to both inductive and capacitive characteristics of circuits 204, 254. In another embodiment, EP1 212 and EP2 214 are distinct conductors—e.g., only indirectly coupled to one another via one or more integrated circuit elements—that do not loop and are to predominantly provide only capacitive (rather than inductive) characteristics of circuits 204, 254. In such an embodiment, circuit 204 (or circuit 254) may be coupled to an external inductor of ophthalmic device 202.

The conditions for generating oscillation by circuit 204 (or circuit 254) may change, for example, according to the amount of resistance $R_{t1}$. Testing may be performed by other circuitry (not shown) of ophthalmic device 200—e.g., by providing an input current and/or voltage and sampling an output at terminals $Term_1$, $Term_2$—to detect for conditions that result in one or more oscillation characteristics. A result of such testing may then be used to determine an amount of overlap by eyelid 230.

Figure 3:
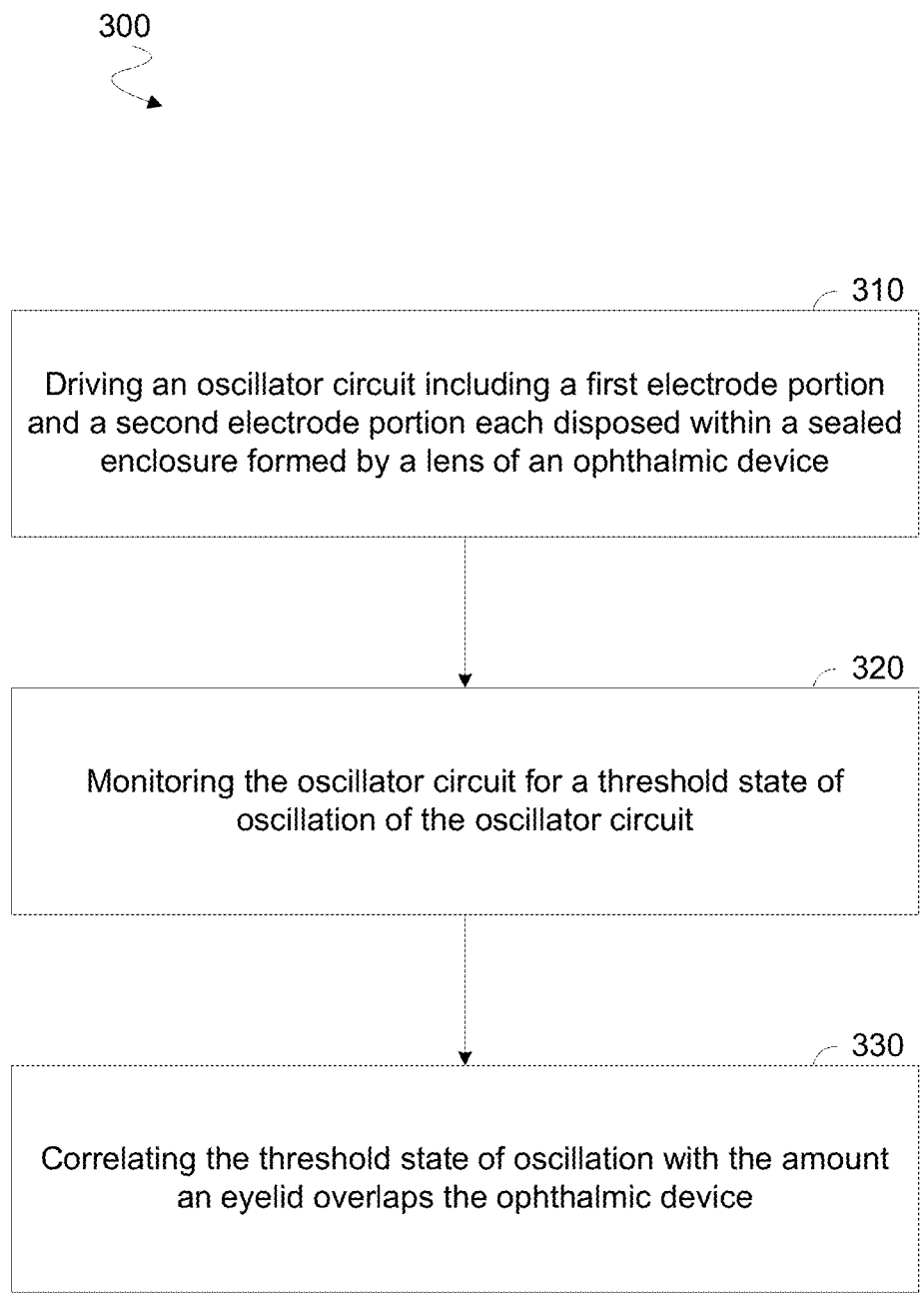
FIG. 3 is a flow diagram illustrating elements of a method to detect, according to an embodiment, overlap of an ophthalmic device by an eyelid of a user.

FIG. 3 illustrates elements of a method 300 to sense an amount of eyelid overlap according to an embodiment. Method 300 may be performed by a device having some or all features of one of ophthalmic devices 100, 140, 202, for example. To illustrate certain features of various embodiments, method 300 is described herein with reference to a sensor system 400 shown in FIG. 4. However, such description may be extended to include performance of method 300 with any of a variety of additional or alternative sensor mechanisms, as variously detailed herein.

Figure 4:
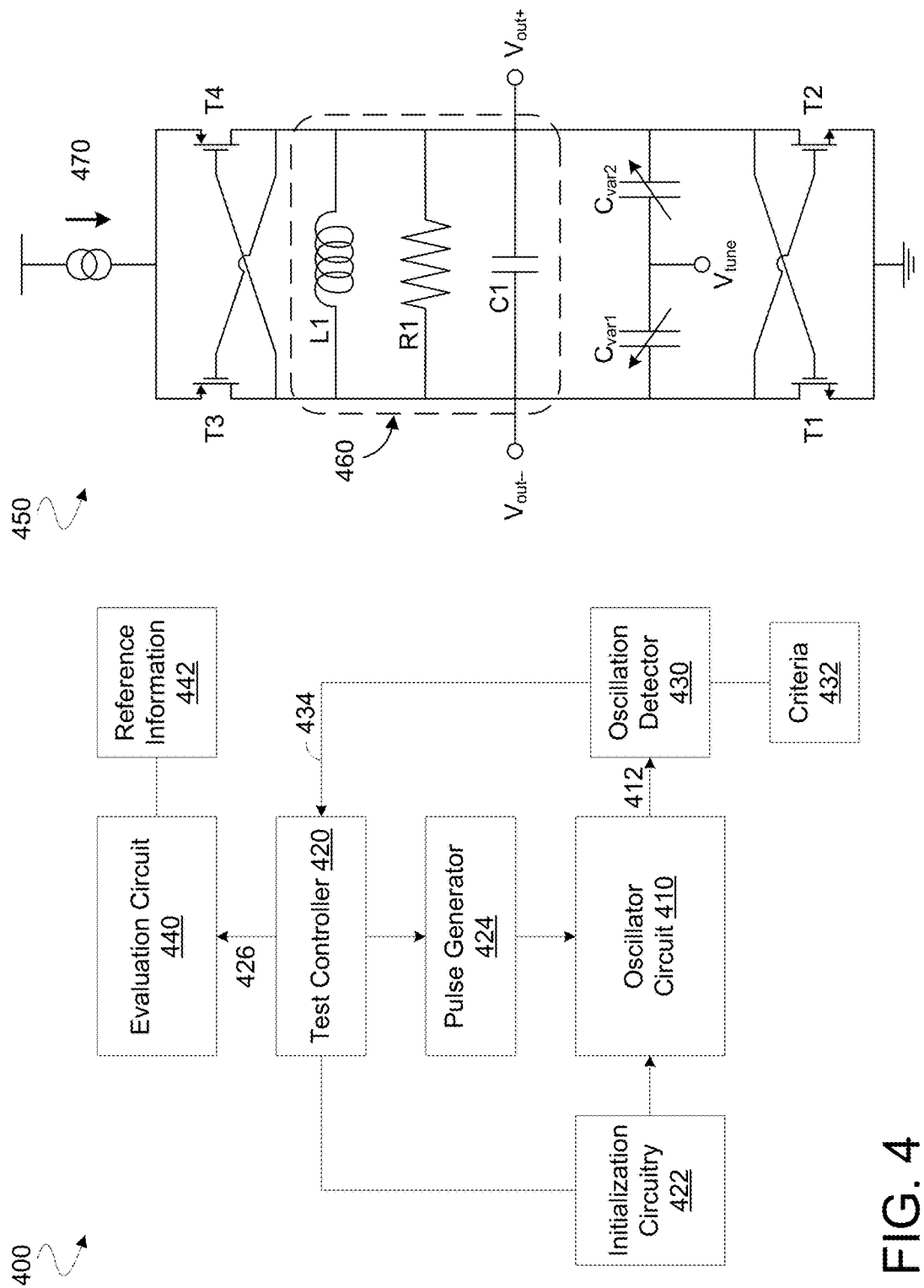
FIG. 4 is a functional block diagram illustrating features of a sensor system to detect eyelid overlap according to an embodiment.

FIG. 4 shows features of a sensor system 400 to detect eyelid overlap according to an embodiment. Sensor system 400 may be adaptable for encapsulation within one or more dielectric enclosure materials (not shown) of a smart contact lens or other ophthalmic device. While the ophthalmic device is mounted on an eye of a user, a first tear film may be disposed by the user over a forward-facing side of the ophthalmic device (e.g., where an eyelid of the user may variously overlap the forward-facing side at different times). A second tear film may be similarly disposed between the ophthalmic device and a cornea of the user's eye.

Method 300 may include, at 310, driving an oscillator circuit which includes a first electrode portion and a second electrode portion each disposed within a sealed enclosure formed by a lens of the ophthalmic device. The first electrode portion and the second electrode portion may be distinct electrodes or, alternatively, different respective portions of a single inductive loop structure. The driving at 310 may result in an electromagnetic field being emitted, with the first electrode portion and the second electrode portion, from the lens and into an environment outside the ophthalmic device. The electromagnetic field may be influenced by an amount to which the first electrode portion and/or the second electrode portion are overlapped by an eyelid of a user wearing the ophthalmic device. In turn, this influence may affect whether the oscillator circuit will exhibit an oscillation response to a perturbation of a given initialization state.

Referring again to FIG. 4, sensor system 400 includes an oscillator circuit 410 that is coupled to conduct charge that facilitates an electromagnetic interaction with structures external to the ophthalmic device—e.g., where such structures include one or more adjoining tear films, a cornea of the user and/or any overlapping portion of the user's eyelid. For example, oscillator circuit 410 may include electrode portions (not shown) extending in a dielectric enclosure material of the ophthalmic device, wherein the dielectric enclosure material facilitates electromagnetic interaction between such electrode portions and at least one or more tear films adjoining the dielectric enclosure material. The electrode portions may variously form any of a variety of structures to facilitate capacitive and/or inductive characteristics affecting such electromagnetic interactions.

For example, the electrode portions may include one or more wire portions (e.g., each having a circular cross-section) and/or one or more structures that each form one or more flat sides. The function of such an electrode portion may be modeled as a plate of a plate capacitor—e.g., wherein a portion of a tear film functions an opposing plate of such a plate capacitor, and wherein an intermediary portion of the dielectric enclosure material may be modeled as a dielectric of such a plate capacitor. In one embodiment, such electrode portions are only indirectly coupled to one another—e.g., at opposite terminals of an inductor and/or via other circuitry that is included in (or coupled to) oscillator circuit 410. Alternatively or in addition, electrode portions of oscillator circuit 410 may be different respective parts of a contiguous conductive loop or loops that extend, for example, near a periphery of the dielectric enclosure material. A conductive loop or loops may function as an inductor of oscillator circuit 410 (and, in some embodiments, may further contribute to capacitance provided with oscillator circuit 410).

In an embodiment, method 300 further comprises, at 320, monitoring the oscillator circuit for a threshold state of oscillation. For example, the driving at 310 may comprise driving the oscillator circuit with a variable current, wherein the monitoring at 320 includes monitoring the oscillator circuit for the threshold state of oscillation while successively changing the variable current.

For example, system 400 may further comprise circuitry to detect an oscillation of oscillator circuit 410, wherein the oscillation is based at least in part on electromagnetic interaction each between a tear film and a respective electrode portion of oscillator circuit 410. In the illustrative embodiment shown, such circuitry (e.g., having features of ODC 114) of system 400 includes a test controller 420, initialization circuitry 422, pulse generator 424 and oscillation detector 430.

The monitoring at 320 may include interrogating the circuit, which in this context refers to testing for an oscillation response (if any) to a particular input bias current. Such interrogating may identify whether a circuit response satisfies one or more evaluation conditions for being considered an oscillation state. In an embodiment, the monitoring at 320 includes successively interrogating the circuit—e.g., where some or all such interrogations each use a different respective amount of the input bias current in attempting to induce circuit oscillation. Adjusting the input bias current—where a next bias current amount is to be set for a next one of the successive circuit interrogations—may be performed intelligently based on one or more previous interrogation results. For example a binary search algorithm (or other search algorithm) may be used to select a next bias current level based at least in part on a result of a most recent circuit interrogation.

FIG. 4 also shows a circuit diagram 450 including RLC oscillator circuitry 460 that models a combination of oscillator circuit 410 and structures, external to an ophthalmic device including system 400, that are to interact electromagnetically with oscillator circuit 410. RLC oscillator circuitry 460—e.g., a model having features of one of circuits 204, 254—comprises an inductor L1, a resistor R1 and a capacitor C1 coupled in parallel with each other between nodes $V_{out-}$, $V_{out+}$. L1 represents an inductance provided by oscillator circuit 410, and R1 represents a combination of resistances variously provided, along different signal paths, within and/or between oscillator circuit 410 and a surrounding environment. C1 represents a combination of capacitances variously provided along some or all such different signal paths. R1 may vary over time based at least in part on an amount by which an eyelid overlaps system 400.

Circuit diagram 450 includes additional circuitry coupled to RLC oscillator circuitry 460, where such additional circuitry facilitates testing to detect eyelid overlap. Such testing may include providing one or more inputs to oscillator circuit 410 and determining whether a resulting oscillation at oscillator circuit 410 takes place—e.g., where the oscillation is based on both the one or more inputs and on interaction between oscillator circuit 410 and a surrounding environment. For example, additional circuitry to provide such one or more inputs may include some or all of a current source 470, circuitry (not shown) coupled to provide a tuning (e.g., biasing) voltage $V_{tune}$ and circuitry (not shown) coupled to operate one or more variable capacitors $C_{var1}$, $C_{var2}$. In the illustrative embodiment shown, circuitry 460 is coupled across terminals nodes $V_{out-}$, $V_{out+}$, as are capacitors $C_{var1}$, $C_{var2}$, cross-coupled transistors T3, T4 and cross-coupled transistors T1, T2. In particular, $V_{tune}$ may be pre-configured, for one or more successive evaluation cycles, to provide for relatively high capacitance values of $C_{var1}$, $C_{var2}$. Such preconfiguring with $V_{tune}$ may result in a relatively high amount of energy being needed to induce oscillation with RLC oscillator circuitry 460. During an evaluation cycle, circuitry such as that of oscillation detector 430 may detect for some minimal amplitude of a signal, across terminals $V_{out-}$, $V_{out+}$, that might be induced with current source 470. In response detecting such a minimal amplitude, the circuitry may signal that $V_{tune}$ is to be pulled higher, thus decreasing the capacitance values of $C_{var1}$, $C_{var2}$. In turn, this decreased capacitance will increase the tendency of RLC oscillator circuitry 460 to continue starting up an oscillation state, and will increase a rate of increase of the amplitude across terminals $V_{out-}$, $V_{out+}$. Such a positive feedback method may facilitate the providing of an oscillation response such as one to be detected by the monitoring at 320.

Based on the monitoring at 320, method 300 may, at 330, correlate a detected threshold state of oscillation with the amount the eyelid overlaps the ophthalmic device. The correlating at 330 may comprise correlating a level of a variable current, bias voltage and/or other condition of an initialization state with the amount the eyelid overlaps the ophthalmic device. For example, predetermined reference information may be accessed, based on the monitoring at 320, to determine a correlation between a particular amount of eyelid overlap and a respective initialization state (or a threshold state of oscillation resulting from perturbation of that respective initialization state).

In some embodiments, the driving at 310 and the monitoring at 320 may be performed multiple times to maintain an up-to-date determination of an amount of eyelid overlap. For example, a level of an input current (such as that provided by current source 470) of a threshold state for enabling circuit oscillation may vary inversely with a change in a resistance due to eyelid overlap. Method 300 may perform multiple test rounds each to detect a respective threshold oscillation state of the oscillator circuit. The test rounds may each include multiple sample cycles each corresponding to a different respective initialization state of the oscillator circuit. The multiple sample cycles may each correspond, for example, to a different respective value of an input to be provided to the circuit. Such an input may include a current (e.g., provided by a current source), a bias voltage and/or the like. In one embodiment, performing the test round includes, for each sample cycle of multiple sample cycles, determining whether an oscillation event results from a perturbation of a corresponding initialization state of the circuit. Determining whether the oscillation event results may include evaluating an amplitude of an output by the circuit based on some threshold minimum amplitude. Alternatively or in addition, determining whether the oscillation event results may include counting transitions by an output of the circuit, and comparing a total number of the counted transitions to a threshold minimum number of transitions.

By way of illustration and not limitation, test controller 420 may include circuitry to coordinate the performance of a test algorithm for evaluating an oscillation response of oscillator circuit 410. A result of such a test algorithm may identify or otherwise indicate a configuration of oscillator circuit 410 (e.g., including respective values of one or more inputs to be provided to oscillator circuit 410) that corresponds to a threshold condition for inducing oscillation with oscillator circuit 410. The test result may thus indicate an affect that a level of a time-varying resistance—the resistance due in part to eyelid overlap—has on oscillation characteristics of oscillator circuit 410.

In one embodiment, test controller 420 operates to implement a test round including multiple successive sample cycles each corresponding to a different respective configuration of oscillator circuit 410 by system 400. For each sample cycle of a test round, test controller 420 may signal to initialization circuitry 422 that oscillator circuit 410 is to be configured with an initialization state corresponding to the sample cycle. In some embodiments, initialization for a given sample cycle includes implementing at oscillator circuit 410 one or more baseline conditions that, for example, are common to all sample cycles of the test round. For example, initialization of oscillator circuit 410 for each sample cycle may include one or more of bringing $V_{tune}$ to a baseline potential (e.g., ground), turning off current source 470, and pulling nodes $V_{out-}$, $V_{out+}$ each to ground or some other baseline potential. Preparing for a sample cycle may further include clearing one or more counters, timers and/or other circuitry that are used to determine a result of the sample cycle.

Subsequently, oscillator circuit 410 may be brought by initialization circuitry 422 from a baseline state to an initialization state that, of the multiple sample cycles of a test round, corresponds to only one such sample cycle. For example, initialization circuitry 422 may set current source 470 to provide a level and/or frequency of current that is for only one sample cycle of the test round. Alternatively or in addition, initialization circuitry 422 may provide at $V_{tune}$ a voltage signal that is specific to one such sample cycle. In some embodiments, one or both of capacitors $C_{var1}$, $C_{var2}$ are configured to provide an amount of a capacitance that is specific to one sample cycle.

After oscillator circuit 410 is put into the corresponding initialization state for a given sample cycle, test controller 420 may induce some perturbation of oscillator circuit 410—e.g., for subsequent sampling to detect whether an oscillation event results from such perturbation. For example, test controller 420 may signal a pulse generator 424 to introduce some spike, step-wave pulse, saw-tooth wave pulse and/or change to an input for oscillator circuit 410. In one embodiment, such a perturbation may be induced at one (e.g., only one) of nodes $V_{out-}$, $V_{out+}$. Alternatively or in addition, perturbation of oscillator circuit 410 may include a spike, pulse or other such change at $V_{tune}$.

Whether oscillator circuit 410 exhibits an oscillation response to such a perturbation may depend in part upon the value of R1 (which in turn depends in part on any eyelid overlap of oscillator circuit 410). An oscillation detector 430 of system 410 may be coupled to detect whether an output of oscillator circuit 410—e.g., a voltage across nodes $V_{out-}$, $V_{out+}$—satisfies a predefined oscillation threshold criteria. For example, a memory of system 400 may store criteria 432 including oscillation threshold information. A predefined oscillation threshold of criteria 432 may include, for example, a minimum number of transitions by a circuit output within a defined time period. Alternatively or in addition, the predefined oscillation threshold may include a minimum amplitude of the circuit output.

In some embodiments, an oscillation threshold includes a threshold frequency (e.g., a minimum frequency that is to qualify as resonance of oscillator circuit 410). For example, as the eyelid overlaps a sensor circuit of an ophthalmic device according to one embodiment, it may affect operation of the sensor circuit by altering an effective inductance and/or capacitance of the nearby environment. Such a change in inductance and/or capacitance may manifest as a change in a resonant frequency of the sensor circuit. Some embodiments variously sense eyelid overlap by detecting for a threshold frequency, a change in resonant frequency and/or the like. Although some embodiments are not limited in this regard, such detecting may be performed in combination with the detecting of a threshold current to start up a circuit oscillation.

Oscillation detector 430 may include one or more counters, frequency-to-amplitude converters, rectifiers and/or other circuitry—e.g., adapted from any of a variety of conventional techniques for detecting oscillation of a voltage and/or a current. For example, oscillation detector 430 may include counter circuitry coupled to count transitions by a voltage across nodes $V_{out-}$, $V_{out+}$. Such counter circuitry may, during a given sampling period, count up-down and/or down-up transitions through a threshold voltage level.

Oscillation detector 420 may determine whether (or not) a signal characteristic at oscillator circuit 410 qualifies as being an oscillation event. For example, oscillation detector 420 may compare a number of transitions of an output signal to a threshold minimum number of transitions. Alternatively or in addition, oscillation detector 420 may compare an amplitude of the output signal to a threshold minimum amplitude. Based on such evaluation, oscillation detector 420 may provide to test controller 420 an indication 434 as to whether the corresponding sample cycle resulted in an oscillation event at oscillator circuit 410. Indication 434 may include a Boolean value specifying occurrence/non-occurrence of the oscillation event. Alternatively or in addition, indication 434 may include information identifying a value of a frequency, amplitude and or other characteristic of any such oscillation event.

Based on indication 434, test controller 420 may determine whether the associated sample cycle corresponds to a threshold condition for inducing oscillation with oscillator circuit 410. Alternatively or in addition, test controller 420 may determine based on indication 434 whether and/or how any next sample cycle of the test round is to be performed. In one embodiment, a test round includes sensor system 400 performing a sequence of sample cycles and, for each successive sample cycle of the sequence, incrementally increasing (or alternatively, decreasing) a characteristic of a signal to be input to oscillator circuit 410. For example, test controller 420 may operate initialization circuitry 422 to sequentially step through successively greater (or lesser) values of a current or other input to be provided by current source 470.

In another embodiment, a test round includes sensor system 400 performing a sequence of sample cycles that function as a binary search of a set of values for an input to be provided to oscillator circuit 410. In such a test round, sample cycles are based on the respective mid-points of successively smaller ranges of input values. By way of illustration and not limitation, some first sample cycle of the test round may include providing an input to a circuit—such as oscillator circuit 410—wherein the value of the input (or, for brevity, a "circuit input value") is a value closest to the middle of a first range of possible circuit input values. In such an embodiment, a circuit input value to be used in the next sample cycle may depend on a result of the first sample cycle. For example, the circuit input value to be used in the next cycle sample may be a value closest to the middle of a second range of possible circuit input values. The second range may be selected based on a result of the first sample cycle—e.g., wherein the second range is an upper half of the first range, or a lower half of the first range, depending on whether the first current sample cycle resulted in an oscillation event with oscillator circuit 410.

Based on the correlating at 330, method 300 may generate one or more signals identifying an amount of the eyelid overlap. For example, based on the test round, test controller 420 may provide to evaluation circuit 440 a test result 426 indicating one or more oscillation characteristics of oscillator circuit 410. Test result 426 may identify or otherwise indicate an initialization state that—of multiple initialization states—most closely represents a threshold state for inducing oscillation with oscillator circuit 410. Based on test result 426, evaluation circuit 440 may access reference information 442 which, directly or indirectly, corresponds various circuit initialization states each with a different respective amount of eyelid overlap. For example, reference information 442 may specify or otherwise indicate, for each of different amounts of an input current (e.g., by current source 470), a corresponding level of a resistance—such as resistance R1 of circuitry 460—that is due at least in part to eyelid overlap. Using such correspondences, evaluation circuit 440 may calculate, select or otherwise determine an amount of eyelid overlap corresponding to an amount of resistance that is indicated by test result 426.

Although some embodiments are not limited in this regard, method 300 may further comprise one or more other operations (not shown) to operate the ophthalmic device based on the correlating at 330. For example, method 300 may further comprise determining a gaze direction of the user based, at least in part, upon the threshold state of oscillation. In one embodiment, predefined reference information stored at the ophthalmic device further specifies a correspondence of various amounts of eyelid overlap each with a respective direction of gaze by the user. A lookup of such reference information may be performed, based on the correlating at 330, to determine a direction of gaze that, for example, may correspond to a particular level of accommodation. In such an embodiment, method 300 may further perform adjusting an optical power of an accommodation actuator of the ophthalmic device.

Alternatively or in addition, method 300 may include generating, based on the threshold oscillation state determined, one or more signals indicating a level of dryness of the user's eye. For example, reference information 442 which additionally or alternatively correspond various circuit initialization states each with a different respective level of dryness (e.g., thicknesses of a tear film). Using such correspondences, evaluation circuit 440 may calculate, select or otherwise determine an amount of eye dryness (or wetness) corresponding to an amount of resistance that is indicated by test result 426.

Reference information 442 is provided—e.g., as an a priori input—for storage in a memory that is included in or coupled to system 400. Reference information 442 may be based on a calibration routine including, for example, wireless communication between the ophthalmic device and one or more devices that are remote from the ophthalmic device. For example, a user of an ophthalmic device including system 400 may be prompted to open an eyelid as widely as possible, to close eyelid slowly, to close eyelid entirely, to blink one or more times (e.g., according to a particular blink sequence). During such movements of the eye, system 400 may perform a calibration routine to associate different circuit initialization states each with a respective amount of eyelid overlap. The particular details of such a calibration process may vary according to implementation-specific details, and are not limiting on some embodiments. Similarly, criteria 432 may be made available to system 400 as a priori information. Criteria 432 may be generated based on a calibration routine and/or manufacturer specifications, for example.

FIG. 5A illustrates an eye-mountable device (EMD) 500 including an eyelid overlap sensor mechanism according to an embodiment. EMD 500 may include a smart contact lens that is configured to be mounted on a surface of the cornea of a user's eye. In an embodiment, EMD 500 includes some or all features of one of ophthalmic devices 100, 140, 202—e.g., wherein at least some operation of EMD 500 is according to method 300. EMD 500 includes one or more dielectric enclosure materials 510 that are arranged to form a sealed enclosure. A sensor mechanism of EMD 500 may include integrated circuitry 530 disposed in the sealed enclosure. Integrated circuitry 530 may provide functionality, such as that of sensor system 400, to determine an amount by which an eyelid of a user might overlap at least some portion of EMD 500. Such determining may be based on detection of an oscillation characteristic of a circuit that is configured to interact electromagnetically, via the one or more dielectric enclosure materials 510, with a tear film formed over a surface of EMD 500. The oscillation characteristic may be based in part on—i.e., may vary based on—a resistance that is due to eyelid overlap. In the example embodiment of EMD 500, the circuit includes a electrode portions 522, 524 that are each part of a contiguous conductive loop structure 520 that extends from integrated circuitry 530 and around a center of EMD 500. The conductive loop structure 520 may facilitate both inductance and capacitance that enables oscillation due to interaction between the circuit and structures external to EMD 500.

FIG. 5B illustrates an EMD 550 including an eyelid overlap sensor mechanism according to another embodiment. EMD 550 may include some or all features of one of ophthalmic devices 100, 140, 202, for example. In an embodiment, EMD 550 includes a material 560 arranged to form, at least in part, a sealed enclosure having disposed therein integrated circuitry 580 of a sensor to determine an amount of eyelid overlap. Such determining may be based on detection of an oscillation characteristic of a circuit that, for example, includes electrode portions 570, 572. In one embodiment, electrode portions 570, 572 are only indirectly coupled to one another—e.g., via one or more circuit elements of integrated circuitry 580. Alternatively or in addition, one of electrode portions 570, 572 may coupled via only one end to the other of electrode portions 570, 572—e.g., where electrode portions 570, 572 do not join to form a loop structure. In the arrangement of EMD 500, electrode portions 570, 572 are configured to facilitate parasitic capacitance (e.g., rather than inductance) for enabling signal oscillation. In such an embodiment, the signal oscillation may be further promoted by coupling of electrode portions 570, 572 to an inductor 582 that, for example, is disposed in or on a substrate of integrated circuitry 580.

EMDs 500, 550 may have any of a variety of arrangements of electrode structures, in respective embodiments. By way of illustration and not limitation, an inner edge of conductive loop structure 520—i.e., an edge that is closest to the center of EMD 500—may extend along or outside of (e.g., conform to) a curve having a radius r1. Similarly, an inner edge of electrode portion 570 (and/or an inner edge of electrode portion 572) may extend along or outside of a curve having a radius r2. For example, radius r1 and/or radius r2 may be within a range from 4.0 mm to 6.0 mm—e.g., wherein such a radius is in a range from 4.0 mm to 5.0 mm.

Alternatively or in addition, conductive loop structure 520—and/or one or each of electrode portions 570, 572—may have an average width that, for example, is in a range from 0.05 mm to 0.3 mm (e.g., where such an average width is in a range from 0.07 mm to 0.15 mm). The width of an electrode portion may be measured in a direction that extends radially from a center of an EMD, as illustrated in FIGS. 5A, 5B by the respective widths w1, w2 shown. In some embodiments, an overall length of conductive loop structure 520 (as measured circumferentially around a center of EMD 500) is in a range from 20 mm to 35 mm. An overall length of one of electrode portions 570, 572 may be in a range from 9 mm to 15 mm, for example. In some embodiments, a total area of one side of conductive loop structure 520—e.g., of the side of conductive loop structure 520 that is shown in FIG. 5A—is in a range from 1.25 mm$^2$ to 7.0 mm² (e.g., wherein the total area is in a range from 2.0 mm² to 3.0 mm²). A total area of one of one of electrode portions 570, 572 may be in a range from 0.6 mm² to 3.4 mm², for example.

An inductance provided by conductive loop structure 520 may be, for example, in a range from 20 nanoHenries (nH) to 100 nH (e.g., wherein such inductance is in a range from 30 nH to 50 nH). Alternatively or in addition, a parasitic capacitance provided with conductive loop structure 520— or provided with electrode portions 570, 572—may be in a range from 0.5 pico Farads (pF) to 5 pF (e.g., wherein the capacitance is between 0.75 pF and 3 pF). However, the various example dimensions and circuit characteristics of EMDs 500, 550 are merely illustrative, and may be different in other embodiments according to implementation specific details.

Figure 6:
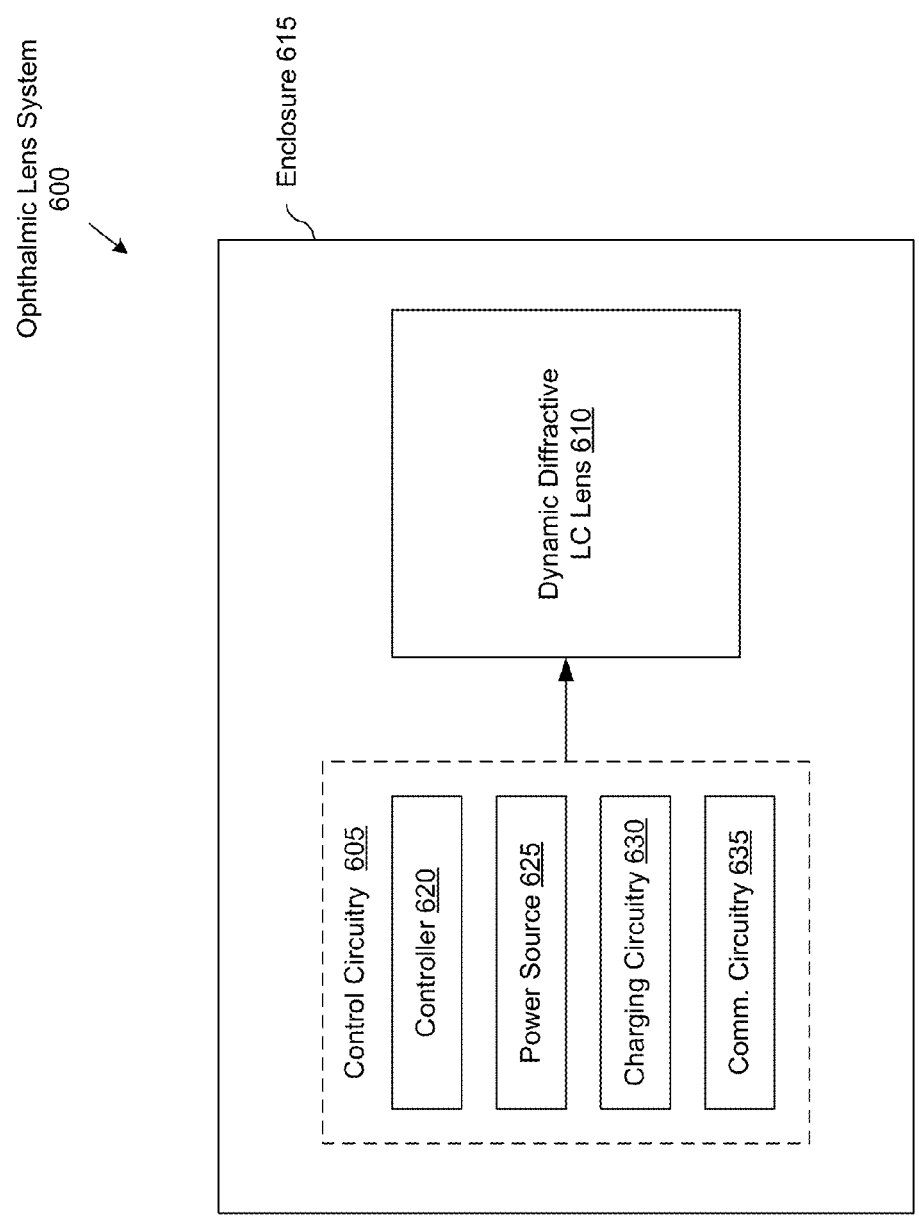
FIG. 6 is a functional block diagram of an ophthalmic lens system including a dynamic diffractive liquid crystal lens, in accordance with an embodiment of the disclosure.

FIG. 6 is a functional block diagram of an ophthalmic lens system 600 including eyelid overlap sensor mechanism in accordance with an embodiment of the disclosure. Ophthalmic lens system 600 may include features of one of ophthalmic devices 100, 140, 202, 500, 550, for example. In an embodiment, ophthalmic lens system 600 includes sensor system 400 and/or performs operations according to method 300.

The illustrated embodiment of ophthalmic lens system 600 includes control circuitry 605, dynamic diffractive liquid crystal ("LC") lens 610, and an enclosure 615. The illustrated embodiment of control circuitry 605 includes a controller 620, a power source 625, charging circuitry 630, and communication circuitry 635.

Ophthalmic lens system 600 may be implemented as a smart contact lens that mounts over a user's eye or as an intraocular lens ("IOL") that may be implanted into the anterior chamber, the posterior chamber, or other locations of the user's eye. In various embodiments, both control circuitry 605 and dynamic diffractive LC lens 610 are disposed within enclosure 615. Enclosure 615 is an optically transmissive material (e.g., transparent, clear, etc.) that seals the internal components and protects the eye. Enclosure 615 may have concave and convex surfaces similar to a contact lens, have generally flat surfaces, or otherwise in various embodiments. In a contact lens embodiment, enclosure 615 may be implemented as a hydrogel or other permeable polymer material that permits oxygen to reach the eye, or non-permeable materials (e.g., glass, plastic, silicon) may also be used. In an IOL embodiment, enclosure 615 may be implemented as a silicon enclosure, or other hermetically sealable materials. Of course, other optically transmissive and biocompatible materials may be used.

Controller 620 includes the logic that coordinates the operation of the other components of ophthalmic lens system 600. Controller 620 may be implemented as hardware logic (e.g., application specific integrated circuit, field programmable gate array, etc.), software/firmware logic executed on a general purpose microcontroller, or a combination of both hardware and software/firmware logic. Power source 625 may be implemented using a variety of power storage devices including a rechargeable battery and/or capacitive elements. Charging circuitry 630 is coupled to power source 625 for charging power source 625 and may include an inductive charging element, a photovoltaic element, a microelectromechanical systems ("MEMS") charging unit that uses natural motion to generate a current, or otherwise. In some embodiments, an energy harvesting antenna (not shown) is coupled to charge power source 625 and/or otherwise provide power for ophthalmic lens system 600. Communication circuitry 635 is coupled to controller 620 to provide external communications therewith. Communication circuitry 635 may include a passive backscatter antenna (e.g., RFID tag) or an active antenna if power budgets permit.

Ophthalmic lens system 600 includes dynamic diffractive LC lens 610 to provide variable optical power that may be dynamically adjusted during operation under the coordination and influence of control circuitry 605. In one embodiment, dynamic diffractive LC lens 610 has two modes of operation each with a different optical power. These modes may be activated under electrical influence from control circuitry 605. In one embodiment, the first mode provides a first optical power for distance vision and the second mode provides a second optical power, different from the first optical power, for short distance vision (e.g., reading or computer monitor distances). In one embodiment, the first mode is a default mode that persists in the absence of an applied voltage while the second mode persists when control circuitry 605 is actively applying a bias voltage to dynamic diffractive LC lens 610. This configuration may provide a failsafe mode where the user's vision defaults to distance vision (e.g., for driving) should control circuitry 605 fail or run out of power.

In an embodiment, controller 620 operates to determine an amount of eyelid overlap based on oscillation characteristics of a circuit structure (not shown) extending in enclosure 615. For example, controller 620 may provide functionality such as that of ODC 114 and/or evaluation circuit 116. An amount of eyelid overlap may be used to determine a direction of gaze by a user. For example, an increased amount of eyelid overlap for an extended period of time may be indicative of a user gazing in a direction that is relatively down and/or inward (toward the user's nose). Such a direction of gaze may be associated by controller 620 with a need for a relatively large level of accommodation to be provided with dynamic diffractive LC lens 610.

Figure 7A:
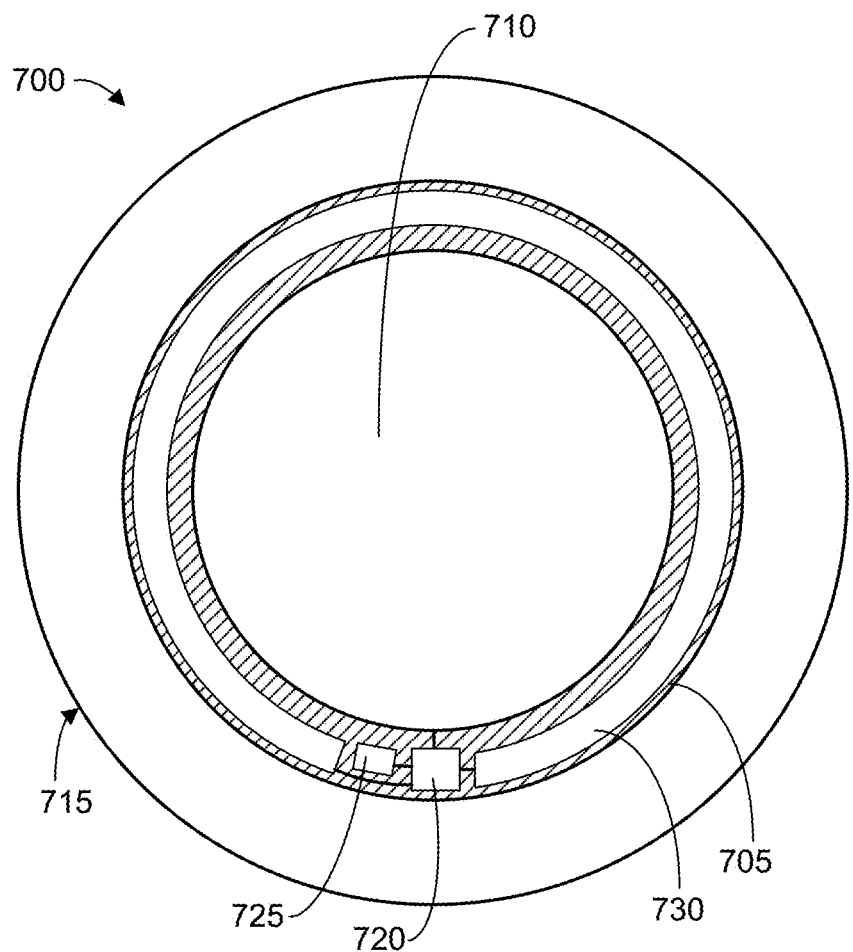
FIG. 7A is a top view of an ophthalmic device, in accordance with an embodiment of the disclosure.
Figure 7B:
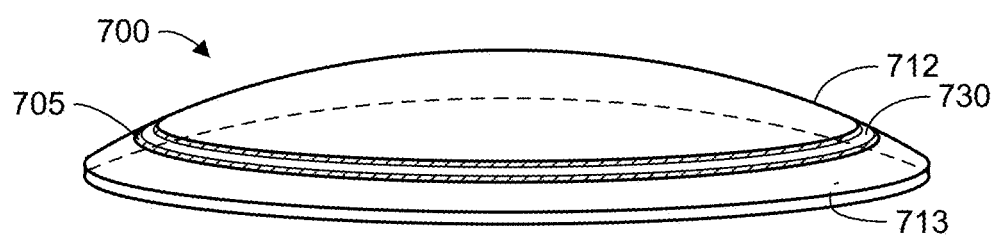
FIG. 7B is a perspective view of an ophthalmic device, in accordance with an embodiment of the disclosure.

FIGS. 7A and 7B are illustrations of a contact lens system 700 including a dynamic diffractive liquid crystal lens, in addition to an eyelid overlap sensor according to an embodiment of the disclosure. Contact lens system 700 is one possible implementation of ophthalmic device 100, for example. The illustrated embodiment of contact lens system 700 includes a substrate 705, a dynamic diffractive LC lens 710, an enclosure 715, a controller 720, a power source 725, and an antenna 730. Enclosure 715 has a size and shape that mounts over the cornea of an eye. In the illustrated embodiment, enclosure 715 includes an external side 712 having a convex shape and an eye-ward side 713 having a concave shape. Of course, contact lens system 700 may assume other shapes and geometries including a piggyback configuration that attaches to a surface of an eye-mountable carrier substrate having an overall shape that resembles a conventional contact lens. Contact lens system 700 may further comprise fully encapsulated electrode structures (not shown), such as those of EMD 500 or EMD 550, coupled to facilitate detection of eyelid overlap according to techniques described herein.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

The following statements provide general expressions of the disclosure herein:

A. An ophthalmic device comprising: a lens forming a sealed enclosure; an oscillator circuit including a first electrode portion and a second electrode portion, the oscillator circuit disposed within the sealed enclosure of the lens; a driver circuit disposed within the sealed enclosure, the driver circuit coupled to drive the oscillator circuit with a signal to cause the first electrode portion and the second electrode portion to emit an electromagnetic field that extends from the lens; an oscillation detector circuit disposed within the sealed enclosure, the oscillation detector circuit coupled to the oscillator circuit to monitor the oscillator circuit for a threshold state of oscillation; and an evaluation circuit disposed within the sealed enclosure, the evaluation circuit coupled to the oscillation detector circuit to receive an indication of the threshold state of oscillation and to correlate the indication of the threshold state of oscillation with an amount of eyelid overlap.

B. The ophthalmic device of statement A, wherein the driver circuit includes: initialization circuitry coupled to successively configure multiple initialization states of the oscillator circuit; a pulse generator coupled to the oscillator circuit, wherein, for each of the multiple initialization states, the pulse generator to provide a respective perturbation of the initialization state, wherein the oscillation detector circuit to monitor the oscillator circuit for the threshold state of oscillation includes the oscillation detector circuit to detect for an oscillation response to the respective perturbation.

C. The ophthalmic device of any of statements A and B, wherein the oscillation detector circuit includes a first memory to store criteria including: a minimum number of transitions by an output from the oscillator circuit within a defined time period, or a minimum amplitude of the output from the oscillator circuit; wherein the oscillation detector circuit to monitor the oscillator circuit for the threshold state of oscillation based on the criteria.

D. The ophthalmic device of statement C, wherein the evaluation circuit includes a second memory to store reference information that corresponds multiple initialization states of the oscillator circuit each with a different respective amount of eyelid overlap.

E. The ophthalmic device of statement A, wherein the first electrode portion and the second electrode portion are different respective portions of an inductive loop structure.

F. The ophthalmic device of statement A, wherein the first electrode portion is coupled to the second electrode portion via only one end of the first electrode portion.

G. The ophthalmic device of statement A, wherein the oscillation detector circuit to perform test rounds each to detect a respective threshold oscillation state of the oscillator circuit, wherein the test rounds each include multiple sample cycles each corresponding to a different respective initialization state of the oscillator circuit.

H. The ophthalmic device of statement G, wherein, for a first test round of the test rounds, the multiple sample cycles of the first test round each correspond to a different respective value of an input to be provided to the oscillator circuit with the driver circuit.

I. The ophthalmic device of statement H, wherein the driver circuit includes a current source, wherein the input includes a current provided by the current source.

J. The ophthalmic device of statement H, wherein the input includes a bias voltage.

K. The ophthalmic device of statement H, wherein the oscillation detector circuit to perform a first test round of the test rounds includes the oscillation detector circuit to select, based on a result of a first sample cycle and a binary search algorithm, a second sample cycle to be performed.

L. A method of operation of an ophthalmic device, the method comprising: driving an oscillator circuit, including a first electrode portion and a second electrode portion each disposed within a sealed enclosure formed by a lens of the ophthalmic device, to emit an electromagnetic field from the first electrode portion and the second electrode portion that is influenced by an amount an eyelid overlaps the ophthalmic device when worn by a user; monitoring the oscillator circuit for a threshold state of oscillation; and correlating the threshold state of oscillation with the amount the eyelid overlaps the ophthalmic device.

M. The method of statement L, wherein driving the oscillator circuit comprises driving the oscillator circuit with a variable current.

N. The method of statement M, wherein monitoring the oscillator circuit for the threshold state of oscillation comprises monitoring the oscillator circuit for the threshold state of oscillation while successively changing the variable current.

O. The method of statement M, wherein correlating the threshold state of oscillation with the amount the eyelid overlaps the ophthalmic device comprises correlating a level of the variable current which corresponds to the threshold state of oscillation with the amount the eyelid overlaps the ophthalmic device.

P. The method of statement L, further comprising: determining a gaze direction of the user based, at least in part, upon the threshold state of oscillation of the oscillator circuit; and adjusting an optical power of an accommodation actuator disposed within the sealed enclosure of the lens in response to the determined gaze direction.

Q. The method of statement L, further comprising performing test rounds each to detect a respective threshold oscillation state of the oscillator circuit, wherein the test rounds each include multiple sample cycles each corresponding to a different respective initialization state of the oscillator circuit.

R. The method of statement Q, wherein performing a first test round of the test rounds includes selecting, based on a result of a first sample cycle and a binary search algorithm, a second sample cycle to be performed.

S. An eye-mountable device (EMD) comprising: a lens forming a sealed enclosure; an oscillator circuit including a first electrode portion and a second electrode portion, the oscillator circuit disposed within the sealed enclosure of the lens; a driver circuit disposed within the sealed enclosure, the driver circuit coupled to drive the oscillator circuit with a signal to cause the first electrode portion and the second electrode portion to emit an electromagnetic field that extends from the lens; an oscillation detector circuit disposed within the sealed enclosure, the oscillation detector circuit coupled to the oscillator circuit to monitor the oscillator circuit for a threshold state of oscillation; and an evaluation circuit disposed within the sealed enclosure, the evaluation circuit coupled to the oscillation detector circuit to receive an indication of the threshold state of oscillation and to correlate the indication of the threshold state of oscillation with an amount of eyelid overlap; an accommodation actuator disposed within the sealed enclosure; and control circuitry to operate the accommodation actuator based on the one or more signals.

T. The EMD of statement S, wherein the driver circuit includes: initialization circuitry coupled to successively configure multiple initialization states of the oscillator circuit; a pulse generator coupled to the oscillator circuit, wherein, for each of the multiple initialization states, the pulse generator to provide a respective perturbation of the initialization state, wherein the oscillation detector circuit to monitor the oscillator circuit for the threshold state of oscillation includes the oscillation detector circuit to detect for an oscillation response to the respective perturbation.

U. The EMD of any of statements S and T, wherein the oscillation detector circuit includes a first memory to store criteria including: a minimum number of transitions by an output from the oscillator circuit within a defined time period, or a minimum amplitude of the output from the oscillator circuit; wherein the oscillation detector circuit to monitor the oscillator circuit for the threshold state of oscillation based on the criteria.

V. The EMD of any of statements S to U, wherein the first electrode portion and the second electrode portion are different respective portions of an inductive loop structure.

W. The EMD of any of statements S to V, wherein the oscillation detector circuit to perform test rounds each to detect a respective threshold oscillation state of the oscillator circuit, wherein the test rounds each include multiple sample cycles each corresponding to a different respective initialization state of the oscillator circuit.

X. The EMD of statement W, wherein the oscillation detector circuit to perform a first test round of the test rounds includes the oscillation detector circuit to select, based on a result of a first sample cycle and a binary search algorithm, a second sample cycle to be performed.

What is claimed is:

1. An ophthalmic device comprising:
a lens forming a sealed enclosure;
an oscillator circuit including a first electrode portion and a second electrode portion, the oscillator circuit disposed within the sealed enclosure of the lens;
a driver circuit disposed within the sealed enclosure, the driver circuit coupled to drive the oscillator circuit with a signal to cause the first electrode portion and the second electrode portion to emit an electromagnetic field that extends from the lens, wherein the driver circuit includes a pulse generator coupled to the oscillator circuit to perturb the oscillator circuit;
an oscillation detector circuit disposed within the sealed enclosure, the oscillation detector circuit coupled to the oscillator circuit to monitor the oscillator circuit for a threshold state of oscillation in response to perturbation from the pulse generator; and
an evaluation circuit disposed within the sealed enclosure, the evaluation circuit coupled to the oscillation detector circuit to receive an indication of the threshold state of oscillation and to correlate the indication of the threshold state of oscillation with an amount of eyelid overlap with the ophthalmic device.

2. The ophthalmic device of claim 1, wherein the driver circuit includes:
initialization circuitry coupled to successively configure multiple initialization states of the oscillator circuit,
wherein the pulse generator is coupled to the oscillation circuit to provide a respective perturbation of each of the multiple initialization states, wherein the oscillation detector circuit is coupled to the oscillation circuit to detect for an oscillation response to each of the respective perturbations.

3. The ophthalmic device of claim 1, wherein the oscillation detector circuit includes a first memory to store criteria including:
a minimum number of transitions by an output from the oscillator circuit within a defined time period, or a minimum amplitude of the output from the oscillator circuit;
wherein the oscillation detector circuit to monitor the oscillator circuit for the threshold state of oscillation based on the criteria.

4. The ophthalmic device of claim 3, wherein the evaluation circuit includes a second memory to store reference information that corresponds multiple initialization states of the oscillator circuit each with a different respective amount of eyelid overlap.

5. The ophthalmic device of claim 1, wherein the first electrode portion and the second electrode portion are different respective portions of an inductive loop structure.

6. The ophthalmic device of claim 1, wherein the first electrode portion is coupled to the second electrode portion via only one end of the first electrode portion.

7. The ophthalmic device of claim 1, wherein the oscillation detector circuit to perform test rounds each to detect a respective threshold oscillation state of the oscillator circuit, wherein the test rounds each include multiple sample cycles each corresponding to a different respective initialization state of the oscillator circuit.

8. The ophthalmic device of claim 7, wherein, for a first test round of the test rounds, the multiple sample cycles of the first test round each correspond to a different respective value of an input to be provided to the oscillator circuit with the driver circuit.

9. The ophthalmic device of claim 8, wherein the driver circuit includes a current source, wherein the input includes a current provided by the current source.

10. The ophthalmic device of claim 8, wherein the input includes a bias voltage.

11. The ophthalmic device of claim 8, wherein the oscillation detector circuit to perform a first test round of the test rounds includes the oscillation detector circuit to select, based on a result of a first sample cycle and a binary search algorithm, a second sample cycle to be performed.

12. A method of operation of an ophthalmic device, the method comprising:
driving an oscillator circuit, including a first electrode portion and a second electrode portion each disposed within a sealed enclosure formed by a lens of the ophthalmic device, to emit an electromagnetic field from the first electrode portion and the second electrode portion that is influenced by an amount an eyelid overlaps the ophthalmic device when worn by a user;

perturbing the oscillator circuit;
monitoring the oscillator circuit for a threshold state of oscillation in response to the perturbing; and
correlating the threshold state of oscillation with the amount the eyelid overlaps the ophthalmic device.

13. The method of claim 12, wherein driving the oscillator circuit comprises driving the oscillator circuit with a variable current.

14. The method of claim 13, wherein monitoring the oscillator circuit for the threshold state of oscillation comprises monitoring the oscillator circuit for the threshold state of oscillation while successively changing the variable current.

15. The method of claim 13, wherein correlating the threshold state of oscillation with the amount the eyelid overlaps the ophthalmic device comprises correlating a level of the variable current which corresponds to the threshold state of oscillation with the amount the eyelid overlaps the ophthalmic device.

16. The method of claim 12, further comprising:
determining a gaze direction of the user based, at least in part, upon the threshold state of oscillation of the oscillator circuit; and
adjusting an optical power of an accommodation actuator disposed within the sealed enclosure of the lens in response to the determined gaze direction.

17. The method of claim 12, further comprising performing test rounds each to detect a respective threshold oscillation state of the oscillator circuit, wherein the test rounds each include multiple sample cycles each corresponding to a different respective initialization state of the oscillator circuit.

18. The method of claim 17, wherein performing a first test round of the test rounds includes selecting, based on a result of a first sample cycle and a binary search algorithm, a second sample cycle to be performed.

19. An eye-mountable device (EMD) comprising:
a lens forming a sealed enclosure;
an oscillator circuit including a first electrode portion and a second electrode portion, the oscillator circuit disposed within the sealed enclosure of the lens;
a driver circuit disposed within the sealed enclosure, the driver circuit coupled to drive the oscillator circuit with a signal to cause the first electrode portion and the second electrode portion to emit an electromagnetic field that extends from the lens, wherein the driver circuit includes a pulse generator coupled to the oscillator circuit to perturb the oscillator circuit;
an oscillation detector circuit disposed within the sealed enclosure, the oscillation detector circuit coupled to the oscillator circuit to monitor the oscillator circuit for a threshold state of oscillation in response to perturbation from the pulse generator;
an evaluation circuit disposed within the sealed enclosure, the evaluation circuit coupled to the oscillation detector circuit to receive an indication of the threshold state of oscillation and to correlate the indication of the threshold state of oscillation with an amount of eyelid overlap;
an accommodation actuator disposed within the sealed enclosure; and
control circuitry coupled to the accommodation actuator and the evaluation circuit to adjust the accommodation actuator based on feedback from the evaluation circuit.

20. The EMD of claim 19, wherein the driver circuit includes:
initialization circuitry coupled to successively configure multiple initialization states of the oscillator circuit,
wherein the pulse generator is coupled to the oscillator circuit to provide a respective perturbation of each of the multiple initialization states, wherein the oscillation detector circuit is coupled to the oscillation circuit to monitor for an oscillation response to each of the respective perturbations.

21. The EMD of claim 19, wherein the oscillation detector circuit includes a first memory to store criteria including:
a minimum number of transitions by an output from the oscillator circuit within a defined time period, or
a minimum amplitude of the output from the oscillator circuit;
wherein the oscillation detector circuit to monitor the oscillator circuit for the threshold state of oscillation based on the criteria.

22. The EMD of claim 19, wherein the first electrode portion and the second electrode portion are different respective portions of an inductive loop structure.

23. The EMD of claim 19, wherein the oscillation detector circuit to perform test rounds each to detect a respective threshold oscillation state of the oscillator circuit, wherein the test rounds each include multiple sample cycles each corresponding to a different respective initialization state of the oscillator circuit.

24. The EMD of claim 23, wherein the oscillation detector circuit to perform a first test round of the test rounds includes the oscillation detector circuit to select, based on a result of a first sample cycle and a binary search algorithm, a second sample cycle to be performed.

25. An ophthalmic device comprising:
a lens forming a sealed enclosure;
an oscillator circuit including an inductive loop electrode, the oscillator circuit disposed within the sealed enclosure of the lens;
a driver circuit disposed within the sealed enclosure, the driver circuit coupled to the oscillator circuit to drive the inductive loop electrode to emit an electromagnetic field that extends from the lens and inductively couples with one or both of a tear film or an eyelid of an eye and establishes an oscillation within the oscillator circuit dependent upon an amount of the eyelid overlapping the ophthalmic device when the ophthalmic device is worn in or on the eye; and
an oscillation detector circuit disposed within the sealed enclosure, the oscillation detector circuit coupled to the oscillator circuit to monitor the oscillator circuit for a threshold state of oscillation, which correlates with the amount the eyelid overlaps the ophthalmic device when worn on the eye.

26. The ophthalmic device of claim 25, wherein the driver circuit comprises:
a current source coupled to the oscillator circuit to drive a current into the oscillator circuit; and
a pulse generator coupled to the oscillator circuit to perturb the oscillator circuit with a pulse signal.

27. The ophthalmic device of claim 26, wherein the driver circuit further comprises:
initialization circuitry coupled to the oscillator circuit to initialize or bias one or more components of the oscillator circuit that influence an onset of the threshold state of oscillation.

* * * * *